ALMOND TREE
Filed July 21 1972
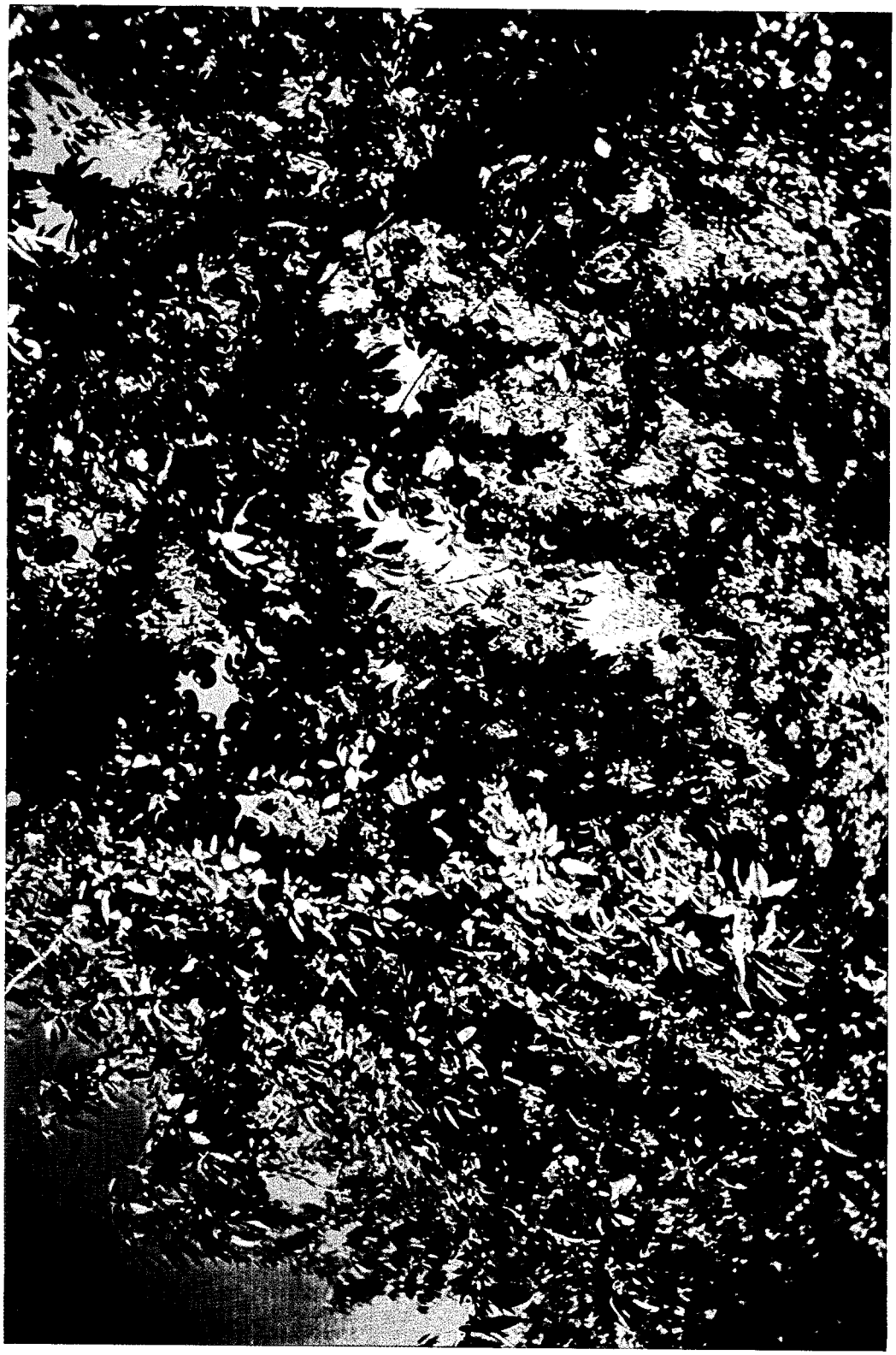

United States Patent Office

Plant Pat. 3,483

Patented Feb. 19, 1974

3,483

ALMOND TREE

Kenneth Stretch, 14010 Le Grand Road, Le Grand, Calif. 95333, and Robert Stretch, 8729 E. Mariposa Way, Merced, Calif. 95340

Filed July 21, 1972, Ser. No. 273,761

Int. Cl. A01h *5/03*

U.S. Cl. Plt.—30 1 Claim

This invention relates to a new and distinct variety of almond tree characterized, as to novelty, by being highly resistant to the effects of frost and diseases.

The variety is more particularly characterized, in comparison with the Nonpareil variety of almond tree, by being more frost resistant, by blooming substantially concurrently therewith and by having larger flowers with more space between petals, and having lesser amounts of pink at the base of each petal than the flowers of the Nonpareil variety. The variety herein claimed is further characterized by a large vigorous, consistent bearing tree having resilient limbs and having substantial tolerance to various diseases including "crazy top," brown rot and shot hole diseases.

The claimed variety of the almond tree was discovered in 1962 in the Stretch Orchards, located at 8729 E. Mariposa Way, Merced, Calif., as a sport of a Nonpareil tree in a row of Nonpareil trees growing in an orchard consisting of Nonpareil, Jordonola and Mission varieties.

A large number of the trees of the claimed variety has been reproduced through grafting and budding operations performed by Robert Stretch and Kenneth Stretch working together in Merced, Calif., on Athlone Road, between Le Grand Road and Mariposa Way, and at 14010 Le Grand Road and 4131 South Minturn Road, Le Grand, Calif.

In 1968 the claimed variety growing in an orchard containing Nonpareil and other varieties produced a large crop when crops from substantially all other varieties in the immediate vicinity of the herein claimed variety were lost due to effects of frost. The claimed variety has produced crops through a number of seasons and does not appear to be susceptible to alternate bearing, and "crazy top" has not appeared in the parent tree or in trees produced from the parent tree. Further, brown rot and shot hole diseases appear to be nonexistent in the claimed variety.

The drawing comprises an illustration, by photographic reproduction, in color, of the claimed variety of almond tree depicting the size and vigor of the tree, the resiliency of the limbs, and its heavy production.

Referring now more specifically to the botanical details of this new and distinct variety of almond tree, the following is an outline description thereof; all color designations being by reference to the Nickerson Color Fan, except where common terms of color definition are employed:

Tree:
- *Size.*—Large, similar to the Nonpareil.
- *Vigor.*—Vigorous, similar to the Nonpareil.
- *Density.*—Open, similar to the Nonpareil.
- *Figure.*—Uniform, similar to the Nonpareil.

Trunk:
- *Form.*—Uniform, similar to the Nonpareil.
- *Texture.*—Medium, similar to the Nonpareil.

Branches:
- *Resiliency.*—Highly resilient, substantially no breakage.
- *Size.*—Large, similar to the Nonpareil.
- *Texture.*—Medium, similar to the Nonpareil.

Lenticels:
- *Number.*—Approximately 28 to 30 per square inch.
- *Size.*—Approximately one quarter inch long.

Foliage:
- *Quantity.*—Abundant, uniformly distributed.

Leaves:
- *Size.*—Large, slightly larger than the Nonpareil. Average length—3½" to 4". Average width—approximately one inch.
- *Shape.*—Oblong, lanceolate in form with an obtuse base and an acuminate tip.
- *Color.*—Dark Green, slightly darker than the Nonpareil.
- *Marginal form.*—Similar to the Nonpareil.
- *Petiole.*—Similar to the Nonpareil in length and thickness.
- *Stem glands.*—Average in number.

Flower buds:
- *Size.*—Slightly larger than the Nonpareil.
- *Shape.*—More elliptic than round.

Flowers:
- *Amount of bloom.*—Very heavy.
- *Blooming period.*—Concurrent with the blooming period of the Nonpareil.
- *Size of flower.*—Larger than those of the Nonpareil and having more space between petals of greater length than those of the Nonpareil.
- *Color.*—Substantially white with small amounts of pink at the base of each petal; as compared with the Nonpareil blossom, each petal has much less pink at the base thereof.
- *Pistil.*—Markedly longer than those of the Nonpareil; the pistils stand approximately 1/16 to 3/16 inch above the stamens and appear to be quite sturdy.

Crop:
- *Bearing.*—Consistent.
- *Maturity.*—Ripens uniformly throughout the tree.
- *Harvest period.*—A few days after the Mission variety.
- *Productivity.*—Heavy.
- *Distribution of nuts on tree.*—Well distributed throughout.
- *Tenacity.*—Hangs well on tree, easy to harvest mechanically, and easy to hull.

Hull:
- *Outer surface.*—Smooth.
- *Form.*—Regular.
- *Thickness.*—Thin.
- *Color at harvest*—Dark greenish yellow (10Y 6/7).
- *Splitting.*—Along suture.
- *Dehiscense.*—Opens freely.

Nut:
- *Size.*—Medium to large; average length—1½"; average width—¾" in the suture plane; an average thickness—½", in the plane normal to suture plane.
- *Form.*—Uniform; length/width—elongate; width/thickness—slightly greater width than thickness.
- *Shell.*—Hard; well sealed.
- *Color.*—Strong Orange Yellow (10YR 7/10).
- *Base.*—Curvate.
- *Stem scar.*—Medium.
- *Apex.*—Obtuse, lanceolate.
- *Tip.*—Recurvate.
- *Inner surface.*—Light.
- *Ventral streak.*—Dark; broad; lanceolate.
- *Suture.*—Closed.

Kernels:
- *Size.*—Medium to large; average length—1"; average width—½"; average thickness—⅜".
- *Form.*—Length/width—elongate; width/thickness—slightly greater width than thickness.
- *Base.*—Curvate.
- *Stem scar.*—Medium.

*Apex.*—Lanceolate.
*Surface.*—Furrowed.
*Pubescence.*—Nil.
*Pellicle.*—Thin.
*Color.*—Brownish Orange (5YR 5/8).
*Number of doubles.*—Numerous.
*Defective kernels.*—None to few.
*Flavor.*—Normal.
*Quality.*—Good.

The tree of the herein claimed variety may vary slightly due to climatic and soil conditions under which the variety is grown. However, the description of the variety is as it is grown in the Central Valley of California.

Having thus described and illustrated our new variety of almond tree, what is claimed as new and desired to be secured by Letters Patent is:

1. A new and distinct variety of almond tree, substantially as illustrated and described, characterized by being highly resistant to frost and of vigorous growth and having high production characteristics; and further characterized when compared with the Nonpareil variety, by being more frost resistant, having resilient limbs and substantially larger flowers with more space between the petals thereof, with lesser amounts of pink at the base of each petal than the flowers of the Nonpareil variety.

No references cited.

ROBERT E. BAGWILL, Primary Examiner